(12) United States Patent
Kong et al.

(10) Patent No.: US 6,476,604 B1
(45) Date of Patent: Nov. 5, 2002

(54) METHOD AND APPARATUS FOR IDENTIFYING HIGH METAL CONTENT ON A SEMICONDUCTOR SURFACE

(75) Inventors: Sik On Kong, Singapore (SG); Tsui Ping Chu, Singapore (SG)

(73) Assignee: Chartered Semiconductor Manufacturing Ltd., Singapore (SG)

( * ) Notice: Subject to any disclaimer, the term of this patent is extended or adjusted under 35 U.S.C. 154(b) by 0 days.

(21) Appl. No.: 09/290,919

(22) Filed: Apr. 12, 1999

(51) Int. Cl.[7] .......................... G01V 3/08; G01N 27/72; G01B 11/00; H01L 21/66
(52) U.S. Cl. ...................... 324/236; 324/633; 324/637; 324/234; 356/372; 438/17
(58) Field of Search ................. 324/71.5, 230, 324/234, 236, 237, 238, 633, 637, 655, 719, 765; 216/86; 331/65; 361/180; 438/10, 14, 17, 18; 427/8; 356/372

(56) References Cited

U.S. PATENT DOCUMENTS

| | | | | |
|---|---|---|---|---|
| 3,064,184 A | * | 11/1962 | Watkiss | 324/230 |
| 3,077,858 A | * | 2/1963 | Ulug | 324/230 X |
| 3,450,985 A | * | 6/1969 | Lorenzi et al. | 324/230 |
| 3,576,525 A | * | 4/1971 | Prucha | 331/65 X |
| 4,000,458 A | * | 12/1976 | Miller et al. | 324/719 X |
| 4,526,177 A | * | 7/1985 | Rudy et al. | 324/236 X |
| 4,847,552 A | * | 7/1989 | Howard | 324/236 X |
| 5,034,704 A | * | 7/1991 | Tomioka et al. | 324/236 X |
| 5,364,510 A | | 11/1994 | Carpio | 204/153.1 |
| 5,552,327 A | | 9/1996 | Bachmann et al. | 437/8 |
| 5,683,180 A | | 11/1997 | De Lyon et al. | 374/161 |
| 5,820,689 A | | 10/1998 | Tseng et al. | 134/3 |
| 5,840,368 A | | 11/1998 | Ohmi | 427/255.4 |
| 6,072,313 A | * | 6/2000 | Li et al. | 324/655 X |
| 6,108,096 A | * | 8/2000 | Berman | |
| 6,111,414 A | * | 8/2000 | Chatterjee et al. | 324/633 |

* cited by examiner

Primary Examiner—Gerard R. Strecker
(74) Attorney, Agent, or Firm—George O. Saile; Rosemary L. S. Pike

(57) ABSTRACT

A new method and apparatus for detecting and measuring the level of metal present on the surface of a substrate is achieved. Energy, in the form of rf or light or microwave energy, is directed at the surface of a wafer, the reflected energy or the energy that passes through the semiconductor substrate is captured and analyzed for energy level and/or frequency content. Based on this analysis conclusions can be drawn regarding presence and type of metal on the surface of the wafer. Furthermore, by inclusion of metal within the resonating circuit of an rf generator changes the frequency of the vibration and therefore detects the presence of metal.

12 Claims, 3 Drawing Sheets

METHOD AND APPARATUS FOR IDENTIFYING HIGH METAL CONTENT ON A SEMICONDUCTOR SURFACE

BACKGROUND OF THE INVENTION (1) Field of the Invention

The invention relates to the field of semiconductor wafer manufacturing, and more specifically to methods of preventing partially processed wafers that have to be reworked from contamination front-end operations of the manufacturing line.

(2) Description of the Prior Art

Semiconductor wafer processing typically is a complex process including a large number and variety of processing steps. These processing steps are, during each of the sequences that are executed as part of the step, closely monitored and may result in a complex web of rework, rejects, partial rework, etc. This leads not to the ideal processing sequence where a wafer proceeds from known step to known step but can result in many diverse flows of partially completed wafers. Wafers may be returned to prior processing steps causing concerns of wafers further down the processing line being contaminated with wafers that have already undergone more advanced steps of processing. It is therefore important to screen for such occurrences and to limit or eliminate the impact of contamination that may be introduced into a wafer processing operation by wafers that are not part of the regular wafer processing flow.

During normal wafer processing, meticulous attention is paid to obtaining and maintaining a clean and particle free environment. This clean environment has a direct impact on wafer yield and therefore on wafer cost. Wafer processing by its very nature tends to introduce impurities into the processing environment, these impurities can for instance be introduced from wafer processing furnaces. Dependent on the type of particle, these particles may diffuse into the semiconductor substrate, especially in areas of the manufacturing process where high frequency operations are being performed on the substrate. This can have a severe detrimental effect on wafer properties making these wafers unsuitable for further use. In other cases, donor or acceptor dopants may be introduced to substrates. These dopants can have a direct affect on the performance of the devices that are at a later stage to be created from these wafers. Yet other impurities can cause surface defects in the surface of the wafer or stacking faults or dislocations in the atomic structure of the substrate. Poor wafer surface can be caused by organic matter that is present in the wafer-processing environment, such as oil or oil related matter.

All of these impurities must be carefully monitored and controlled and must, when present, be removed from the wafer processing environment. This control must be exercised within the cycle of wafer processing steps and at the beginning of the wafer processing process. The frequency and intensity of such contaminant control operations is highly cost dependent and should, wherever possible, be performed at as low a cost as can be accomplished. These methods of identification and elimination must therefore be simple but yet effective.

To start wafer processing with wafers that are free of contaminants, loose particles are typically first removed from the wafers by means of a wafer scrubbing process. In this way various dusts (atmospheric, silicon and quartz), photoresist chunks and bacteria are removed. Where very small particles are to be removed this is usually accomplished by a polishing operation.

Organic impurities such as hydrocarbons and greases are, after the cleaning process, removed with the use of solvents such as trichloroethylene, acetone, p-xylene, methanol and ethanol. A final cleaning can then be performed using various inorganic chemicals to remove heavy metals, for example. These inorganic chemical mixtures are strong oxidants, which form a thin oxide layer at the wafer surface. This oxide layer is stripped, removing impurities absorbed into the oxide layer.

Also used to further enhance wafer cleaning can be conventional chemical cleaning operations that include acid and rinse baths. These processes remove chemically bonded film from the surface of the wafer.

A further cleaning operation includes the use of mechanical scrubbing operations. These operations tend to be aggressive cleaning operations that use polishing pads affixed to turning tables that hold the substrate that is being polished. Due to the nature of this cleaning operation, the operation needs to be carefully monitored and special precaution needs to be taken to assure that particles that are removed during the operation are removed from the environment.

Typically, the turntable is rotated at various controlled speeds, for instance 10 to 100 RPM, in a controlled clockwise or counterclockwise direction. A silicon wafer, generally in the form of a flat, circular disk, is held within a carrier assembly with the substrate wafer face to be polished facing downward. The polishing pad is typically fabricated from a polyurethane and/or polyester base material.

Another field in the high density interconnect technology is the physical and electrical interconnection of many integrated circuit chips to a single substrate commonly referred to as a multi-chip module (MCM). A multi-layer structure is created on the substrate in order to achieve a high wiring and packing density. This multi-layer structure allows for short interconnects and improved circuit performance. Separation of the planes within the substrate, such as metal power and ground planes, is accomplished by separating the layers with a dielectric such as a polyimide. Metal conductor lines can be embedded in other dielectric layers with via openings that provide electrical connections between signal lines or to the metal power and ground planes.

In the indicated processes, great care is used to assure that the surfaces of interfaces have good planarity. In a multi-layer structure, a flat surface is extremely important to maintain uniform processing parameters from layer to layer. Layer dependent processing greatly increases processing complexity. Many approaches to producing a planar surface have been incorporated into methods of fabricating high density interconnects and integrated circuit chips in the past. For instance, the lines and vias can be planarized by applying multiple coatings of polyimide which are used to achieve an acceptable degree of planarization. Application of multiple coatings of thick polyimide is however time consuming and creates high stress on the substrate.

The problems associated with prior art polyimide processes have become more troublesome. For example, one of the main difficulties with polyimide processes is that the profiles (i.e. slopes) of the polyimide at the bonding pad edges are not consistent. Rough edges or films having numerous flakes and other defects are pervasive throughout the prior art. In other cases, pieces of photoresist can sometimes become deposited on the surface of the bonding pads causing spikes of unetched passivation layer to be left behind on the bonding pad itself. Although these problems have not prevented the use of conventional polyimide processes in conjunction with standard wire bonding techniques, these shortcomings are unacceptable in the newer, more advanced bonding.

All of the above indicated processing conditions and environments can lead to the introduction of a large number of contaminants and therefore lead to the need for strict control of the environment and the way in which the wafers that are being processed are being routed. Among the contaminants that can accumulate on the surface of a substrate are metals such as copper or aluminum. Control mechanisms that enhance the monitoring of the level of metal deposited on the surface of a wafer prevent unnecessary re-routing and rework of such wafers. Production cost of semiconductor wafers will be reduced if such wafers can be identified so that only wafers that need to be rerouted for rework are entered into the rework cycle.

U.S. Pat. No. 5,820,689 (Tseng et al.) discloses a wet chemical treatment system.

U.S. Pat. No. 5,552,327 (Bachmann et al.) shows a method for monitoring etching using reflectance spectroscopy.

U.S. Pat. No. 5,840,368 (Ohmi) shows a furnace system.

U.S. Pat. No. 5,683,180 (De Lyon et al.) shows a method of wafer temperature measurement using reflectivity spectroscopy.

U.S. Pat. No. 5,364,510 (Carpio) shows a scheme for bath chemistry control.

SUMMARY OF THE INVENTION

It is the primary objective of the invention to identify semiconductor substrates that contain metal on the surface of the substrate.

It is a further objective of the invention to inhibit incorrect routing of wafers.

It is a further objective of the invention to eliminate unnecessary substrate rework activities.

It is a further objective of the invention to reduce the overall cost of substrate manufacturing.

It is yet another objective of the invention to reduce human error in the identifying and routing of substrates in the substrate manufacturing process.

It is yet another objective of the invention to reduce the workload for front-end cleaning sinks and furnaces.

It is yet another objective of the invention to prevent mixing of rework wafers with regular wafer processing flow.

It is yet another objective to prevent unnecessary wafer scrapping due to suspected metal contamination.

In accordance with the objectives of the invention, a new method of detecting and measuring the level of metal present on the surface of a substrate is achieved. A wafer can, at any time and at any location within the wafer processing cycle, be measured for the existence of metal on the surface of the layer. The presence of metal causes the raising of a visual or audible alarm thereby invoking human or automatic intervention.

Under the first embodiment of the invention, rf power is directed at the surface of a wafer, the reflected rf energy is captured and analyzed for intensity and frequency content. Based on this analysis conclusions can be drawn regarding presence and type of metal on the surface of the wafer.

Under the second embodiment of the invention, a source of light exposes the surface of the wafer under an angle such that part of the light reflects off this surface. The reflected light is captured and measured. Based on the measurements obtained in this manner, conclusions can be drawn concerning the reflectivity of the reflecting surface, that is the surface of the wafer. These conclusions lead directly to a measurement of the amount of metal present on the surface of the wafer.

Under the third embodiment of the invention, a magnetron radiates electromagnetic energy in the frequency range of microwave frequency. This energy is, under an angle, directed at the surface of the wafer that is being evaluated. Part of the energy is reflected by the surface of the wafer, another part passes through the wafer and can be measured after it has passed through the wafer. By comparing the level of the reflected energy with the level of the energy that passed through the wafer, conclusions can be drawn about the reflectivity of the wafer surface and therefore about the amount of metal that is present on the surface of the wafer.

DESCRIPTION OF THE PREFERRED EMBODIMENT

Figure 1:
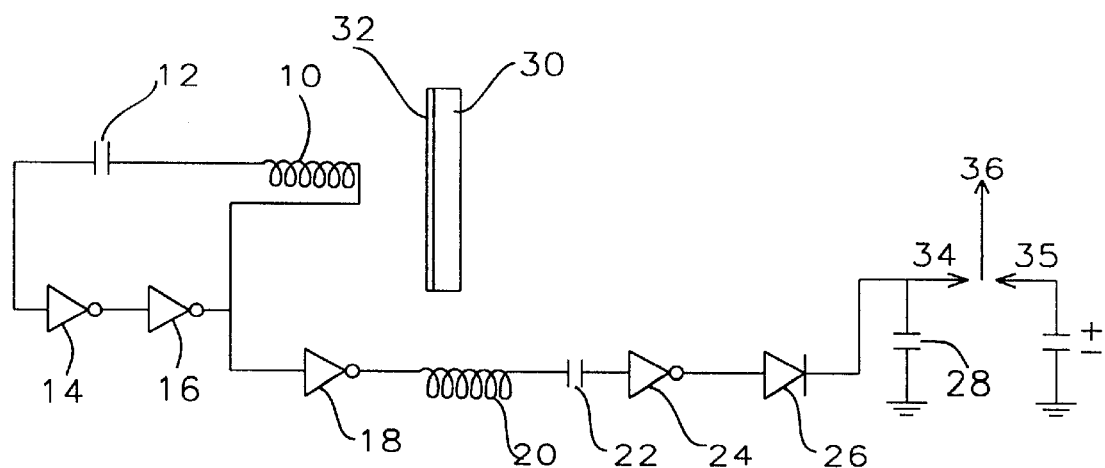
FIG. 1 shows details of the implementation of the first embodiment of the invention, which uses an rf metal detector arrangement to measure the presence of metal on the surface of a wafer.

Referring now specifically to FIG. 1, there is shown an electronic circuit that serves as a means to identify and measure the amount of rf energy that is reflected by the surface of a wafer.

The electronic circuit contains three functional sections: a LC resonating circuit, a LC tuning circuit and a rectifying circuit.

RF energy of a certain frequency is generated by an rf generating circuit that comprises the amplifiers 14 and 16 and the LC tuning components 12 and 10. The resonating rf wave is amplified by amplifier 18 and passes through the second tuning circuit consisting of inductor 20 and capacitor 22. The second tuning circuit 20/22 selects specifically the rf frequency generated by the first tuning circuit 12 and 10. The selected wave is then amplified by amplifier 24 and rectified by diode 26 and capacitor 28 to form a dc signal 34, this dc voltage 34 can be compared with the reference dc voltage 35, comparator 37 providing the means for comparing the dc voltage 34 with the limit voltage level 35.

When a wafer 30 with a metal layer 32 is brought in proximity with the coil 10, the inductance and the stray capacitance of the first resonating circuit changes, causing the dc output voltage to be reduced or to be eliminated. This triggers an alarm and produces a control signal that stops the subsequent action of putting the wafer into a cleaning sink or a furnace, thereby avoiding the contamination.

Element 37 is a means for comparing a dc voltage level 34 with a limit voltage 35. Said means 37 for comparing the voltage level 34 with a predetermined or limit voltage level 35 is determining whether the dc voltage level 34, which is determined by and indicative of the level of the reflected or penetrated rf or microwave energy, is higher, lower or equal to a pre-set or adjustable limit voltage value 35. Element 37 provides an electrical signal 36 that reflects the outcome of this determination. Electrical signal 36 indicates that the result of the compare, a compare that is performed by the means of compare 37, is either a high compare (that is voltage 34 is higher than voltage 35) or an equal compare (that is voltage 34 is equal to voltage 35) or a low compare (that is voltage 34 is lower than voltage 35).

Figures 2A, 2B:
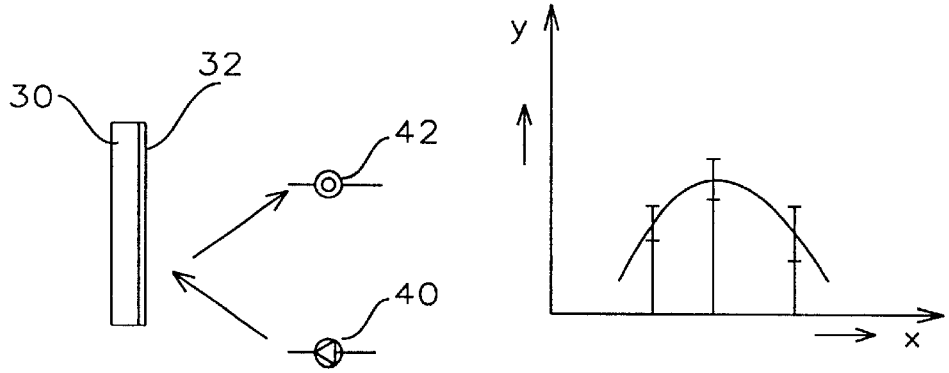
FIGS. 2a and 2b show details of the implementation of the second embodiment of the invention, which uses a light emitting diode for the source of energy that is reflected off the surface of the wafer.

From the diagram that is provided in FIG. 2b the following can be concluded:

- high metal surface content can be identified on the surface of a substrate by providing reflected or penetrated rf or microwave energy; this reflected or penetrated rf or microwave energy is captured by amplifiers 14, 16 and a tuning circuit comprising a capacitor 12 and an inductor 10
- the reflected or penetrated rf or microwave energy comprises rf or microwave energy having a frequency and an amplitude. The reflected or penetrated rf or microwave energy is provided to a rf or microwave energy measurement apparatus, this rf or microwave measurement apparatus is made up of components 18 (an amplifier), 20 (an inductor), 22 (a capacitor), 24 (an amplifier), 26 (a diode) and 28 (a capacitor)
- the surface of a semiconductor substrate is exposed to the source of radiation of rf or microwave energy, thereby including the substrate into the tuning circuit of the rf or microwave generator thereby changing the frequency of the rf or microwave wave due to the metal containing substrate; an rf or microwave energy measurement apparatus captures the rf or microwave wave of changed frequency
- the sources of energy radiation have been highlighted as the Light Emitting diode (LED) 40 in FIG. 2a and as the magnetron 50, FIG. 3, as a source of radiation in the range of microwave frequencies
- the rf or microwave energy measurement apparatus generates a dc voltage 34 that is indicative of the frequency and the amplitude of the reflected or penetrated rf or microwave energy that is provided to the rf or microwave energy measurement apparatus, the reflected or penetrated rf or microwave energy being energy that is reflected by a metal containing surface, as highlighted in FIG. 2a of the instant invention, or energy that has penetrated this surface, as highlighted in FIG. 3 of the instant invention; this dc voltage 34 can be compared with a reference dc voltage 35, providing the means for comparing the dc voltage 34 with the limit voltage level 35
- the source of radiation 40, being a LED in FIG. 2a or a magnetron 50, FIG. 3, is positioned in a stationary and well defined physical location both with respect to the surface of the substrate and with respect to the rf or microwave energy measurement apparatus; the rf or microwave energy measurement apparatus can capture reflected or penetrated rf or microwave energy and can, for each reflected or penetrated rf or microwave frequency including a first and a second reflected or penetrated rf or microwave frequency, measure the energy level of the captured reflected or penetrated energy; from this follows that the frequency of the tuning circuit 10/12 changes from a first reflected or penetrated rf or microwave energy having a first frequency and a first amplitude to a second reflected or penetrated rf or microwave energy having a second frequency and a second amplitude of the rf or microwave waves created by the source of reflected or penetrated rf or microwave energy, due to metal that is present in the surface of the substrate, reflecting the fact that the tuning of an oscillating circuit is affected by the tuning LC components of this circuit; a change in either one of these components of the tuning LC components results in changing the oscillating frequency or rf or microwave energy of the oscillating circuit, thereby comprising changing from a first reflected or penetrated frequency and amplitude to a second reflected or penetrated frequency and amplitude
- the reflected or penetrated rf or microwave energy measurement apparatus is calibrated to provide a dc level output of known value for each particular and unique reflected or penetrated rf or microwave frequency, thereby specifically including a first and a second reflected or penetrated frequency
- the dc voltage 34 is compared with a limit voltage level 35, and
- by determining whether the dc voltage level 34 that is indicative of the reflected or penetrated rf or microwave energy is higher, lower or equal to a pre-set of adjustable limit voltage value 35, the presence or absence of metal on the surface of the substrate can be determined.

By using the wavelengths of the three primary colors (red, green and blue) the amount of light that is reflected by the surface of the wafer (the reflectivity) by these primary colors can be measured (by the photodetector). The three primary colors have unique wavelengths, these wavelengths are indicated as three points on the X-axis of FIG. 2b. The Y-axis of FIG. 2b indicates reflectivity values. The reflectivity values (Y-axis values) measured for the three primary colors (X-axis values) can then be plotted in FIG. 2b. The range of reflectivity values (Y-axis values) is, for a particular metal, known. If therefore the three measurements of reflectivity that have been obtained in the manner indicated fall within the (known) range for a particular metal, the conclusion is clear that the metal that is present on the reflecting surface (the surface of the wafer) is the same metal as the metal that belongs to that range of reflectivity values. Therefore, in measuring the reflectivity for 3 wavelengths, for instance 300, 500 and 700 nm, and if for all three points the measured reflectivity falls within the range of for instance aluminum, the conclusion is apparent that aluminum is present on the surface of the wafer. An automatic response mechanism can be implemented to respond to the presence of aluminum on the surface of the wafer. This can be implemented by using three LED's and three photodiodes and an "and" circuit that gives a signal when the output voltage of all three diodes falls within a specific range of values.

Figure 3:
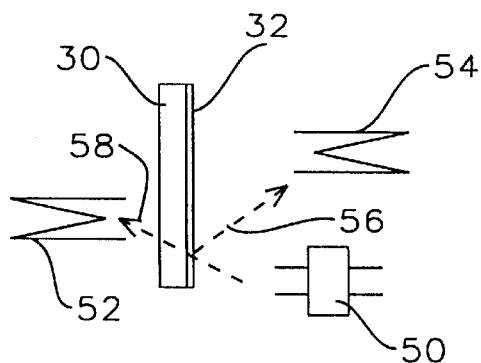
FIG. 3 shows details of the implementation of the third embodiment of the invention, which uses a magnetron for the source of energy that is reflected off the surface of the wafer.

FIG. 3 uses a magnetron 50 as its source of radiation in the range of microwave frequencies. This radiation is again aimed under an angle at the wafer that is being tested. Part 56 of the energy that strikes the surface of the wafer is reflected, part 58 of the energy penetrates the surface of the wafer and can be measured "behind" the wafer. The magnetron 50 is positioned approximately as shown with respect to the position of the wafer, microwave detector 52 measures the energy that has penetrated the wafer, microwave detector 54 measures the energy that is reflected by the surface 32 of the wafer 30. A strong reflection by the surface 32 of wafer 30 indicates the presence of metal on that surface, if therefore detector 54 measures a higher level of microwave energy than detector 52, it is clear that metal is present on the surface of the wafer. Automatic response mechanisms can be implemented that are activated either by the signal from the detector for reflection or by the detector for transmission or by subtracting the signal of one from the other.

Figure 4:
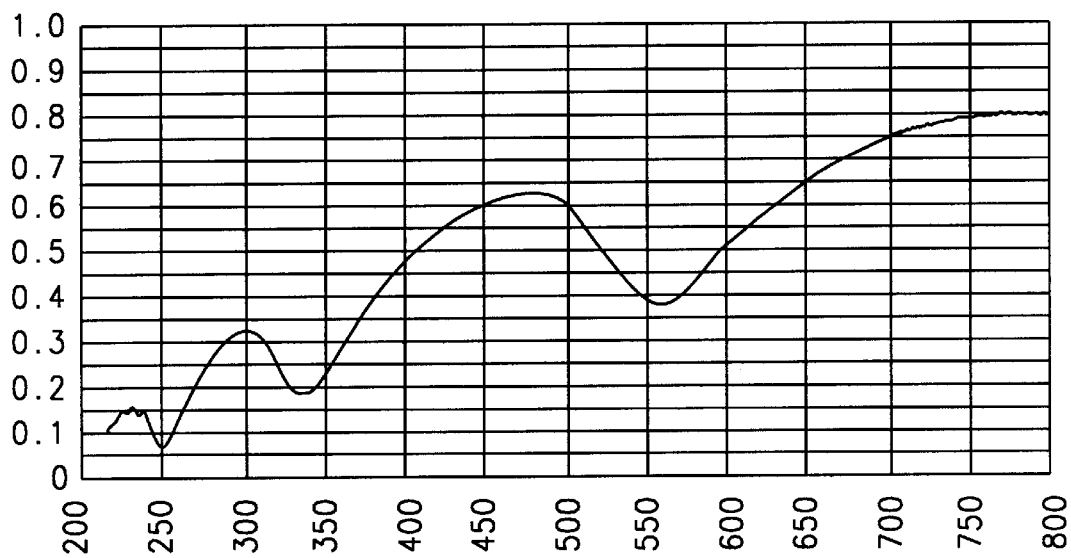
FIG. 4 shows a graph of the reflectivity of a $SiO_2$ layer deposited on Si as a function of wavelength.
Figure 5:
FIG. 5 shows a graph of the reflectivity of a layer of AlCu as a function of wavelength.

FIGS. 4 and 5 further emphasize the basic concept underlying the invention, that is that surface reflectivity is dependent on the type and concentration of the material contained within the reflecting surface and is dependent on the frequency of the wavelength of the energy that is reflected from this surface. Both FIG. 4 and FIG. 5 show the different reflectivity optical light of an $SiO_2$ surface as compared with an aluminum surface. FIG. 4 shows this correlation for a layer of $SiO_2$ that has been deposited on the surface of a layer of Si. FIG. 5 shows this correlation for a layer of AlCu that has been deposited on the surface of a layer of Si. FIGS. 4 and 5 apply to the LED-photodiode method only. It is clear that both correlations have very unique and identifiable characteristics, these characteristics are used as the basis for the invention. Most noteworthy in FIG. 4 is the seesaw nature of the reflectivity of the $SiO_2$ layer as the frequency of the reflected light decreases. FIG. 5 shows that, for AlCu, the reflectivity is and remains at a plateau from where the reflectivity only slowly decreases for relatively high frequencies in the reflected light.

Figure 6A:
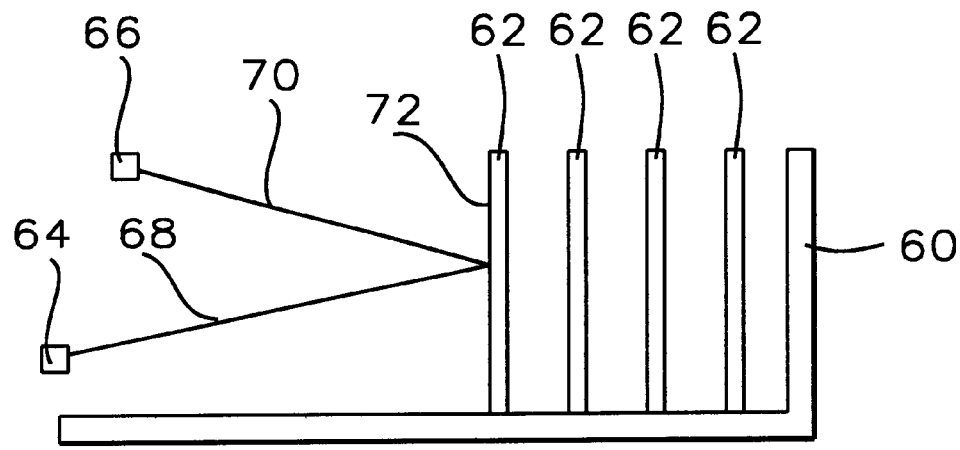
FIGS. 6a and 6b show two possible applications of the invention in re-routing wafers.

FIG. 6a shows a side view of an implementation of the invention that lends itself to automatic handling of wafers based on the amount and type of metal on the surface of the wafer. The metal detector apparatus as described can be mounted as shown, facing the surface of the wafers and linked to a robotic arm that can be used to remove wafers from the teflon wafer holder. The action of removal is triggered by the level of detection reaching a level that indicates the presence of metal, the robotic arm removes the wafer in question and positions that wafer into another wafer carrier for further wafer processing. The operation of identifying contaminated (with metal) wafers is thereby automated and removed from human intervention and human error. Wafers 62 are mounted in the wafer carrier 60, the source of energy 64 broadcasts the energy 68 to the surface 72 of the wafer 62, part 70 of the energy is reflected by the surface 72 and detected by the energy detector 66. This energy detector can readily determine the presence and type of metal, if any, which is present on the surface 72 of wafer 62.

Figure 6B:
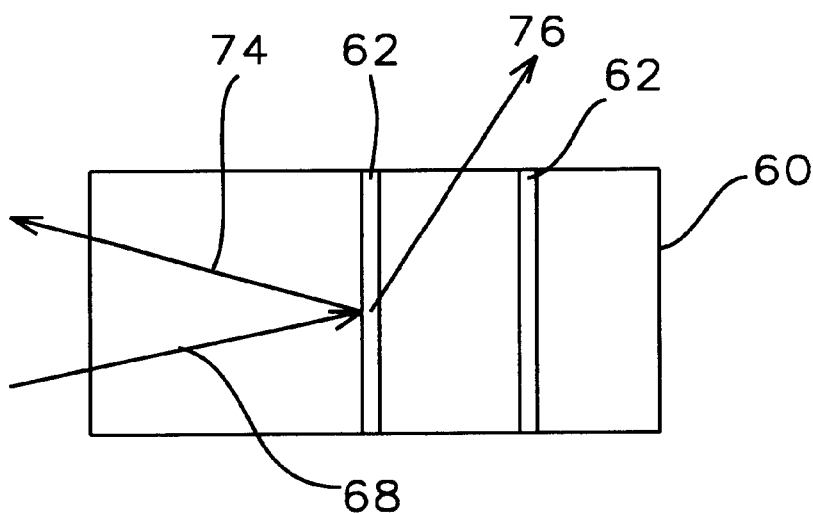

FIG. 6b shows a top view of a similar arrangement that allows the application of using a magnetron as source of energy whereby the incident radiated energy 68 is partially reflected (74) by the surface of the wafer 62 and partially transverses (76) the wafer. Wafers 62 are mounted in the wafer carrier 60. By measuring and comparing the reflected energy 74 with the penetrated energy 76, conclusions can be drawn regarding the presence and type on metal on the surface of the wafer.

For the applications of the invention as shown in FIGS. 6a and 6b, methods known in the art of wafer processing and wafer handling can be applied for removing wafers that have undesirable surface coatings of metal. These wafers, once removed from the normal wafer processing flow, can then be handled in accordance with required procedures established for such wafers.

Although the present invention is illustrated and described herein as embodied in the construction of a number of examples, it is nevertheless not intended to be limited to the details as presented. Rather, various modifications may be made in the details within the scope and range of equivalents of the claims and without departing from the spirit of the invention.

What is claimed is:

1. A method for identifying high metal surface content substrate, comprising the steps of:
   providing a semiconductor substrate, said substrate having a surface;
   providing a source of rf energy, said source of rf energy providing rf waves having a frequency and an amplitude, said source of rf energy having a rf tuning circuit;
   providing a rf energy measurement apparatus, said rf energy measurement apparatus being able to generate a dc voltage that is indicative of the frequency and the amplitude of said rf energy provided by said source of rf energy;
   exposing the surface of said semiconductor substrate to said source of rf energy thereby including the surface of said substrate into the tuning circuit of the source of rf energy, changing the a first rf energy having a first frequency and a first amplitude of the rf energy created by said source of rf energy to a second rf energy having a second frequency and a second amplitude of the rf waves created by said source of rf energy due to metal being present in the surface of said substrate;
   entering said second rf energy into said rf energy measurement apparatus, said rf energy measurement apparatus creating a dc voltage level indicative of said second rf energy;
   providing a dc reference voltage level;
   comparing said dc voltage level created by said energy measurement apparatus which is indicative of said second rf energy with said dc reference voltage level; and
   determining if said dc voltage level created by said energy measurement apparatus is below or equal to said dc reference voltage level.

2. The method of claim 1 whereby said source of radiation of rf energy creates electrical energy within a rf frequency range, whereby furthermore said source of energy is positioned in a stationary location with respect to the surface of said substrate.

3. The method of claim 1 wherein said rf energy measurement apparatus measures rf energy, whereby said rf energy measurement apparatus is calibrated to provide a dc voltage of known value for each rf frequency and for each configuration of location and orientation between said source of rf energy and the surface of said substrate.

4. The method of claim 1 whereby said exposing the surface of said semiconductor substrate to said source of rf energy is exposing the active side of said semiconductor substrate to said rf tuning circuit of said source of rf energy.

5. The method of claim 1 wherein said entering said second rf energy into said rf energy measurement apparatus is creating a dc voltage level that is directly proportional to and indicative of a metal content on the surface of said substrate, said dc voltage level being available to activate a device, invoking human intervention.

6. The method of claim 1 wherein said comparing said dc voltage level with a dc reference voltage level is determining whether said dc voltage level that is indicative of said second rf energy is higher, lower or equal to said dc reference voltage value, thereby providing an electrical signal that reflects the outcome of said determination, said electrical signal being indicative of the result of said compare being either a higher compare or an equal compare or a lower compare.

7. An apparatus for identifying high metal surface content substrate, comprising:
- a source of rf energy, said source of rf energy providing rf waves having a frequency and an amplitude, said source of rf energy having a rf tuning circuit;
- a rf energy measurement apparatus, said rf energy measurement apparatus being able to generate a dc voltage that is indicative of the frequency and the amplitude of said rf energy provided by said source of rf energy;
- a means for exposing the surface of a semiconductor substrate to said source of rf energy by including the surface of said substrate into the tuning circuit of the source of rf energy, changing a first rf energy having a first frequency and a first amplitude of the rf energy created by said source of rf energy to a second rf energy having a second frequency and a second amplitude of the rf waves created by said source of rf energy due to metal being present in the surface of said substrate;
- a means for entering said second rf energy into said rf energy measurement apparatus, said rf energy measurement apparatus creating a dc voltage level indicative of said second rf energy;
- a dc reference voltage level;
- a means for comparing said dc voltage level created by said energy measurement apparatus which is indicative of said second rf energy with said dc reference voltage level; and
- a means for determining if said dc voltage level is above or equal to said reference dc voltage level.

8. The apparatus of claim 7 whereby said source of radiation of rf energy creates electrical energy within a rf frequency range, whereby furthermore said source of energy is positioned in a stationary location with respect to the surface of said substrate.

9. The apparatus of claim 7 wherein said rf energy measurement apparatus measures rf energy, whereby said rf energy measurement apparatus is calibrated to provide a dc voltage of known value for each rf frequency and for each configuration of location and orientation between said source of rf energy and the surface of said substrate.

10. The apparatus of claim 7 whereby said means for exposing the surface of said semiconductor substrate to said source of rf energy is exposing the active side of said semiconductor substrate to said rf tuning circuit of said source of rf energy.

11. The apparatus of claim 7 wherein said means for entering said second rf energy into said rf energy measurement apparatus is creating a dc voltage level that is directly proportional to and indicative of a metal content on the surface of said substrate, said dc voltage level being available to activate a device, thereby invoking human intervention.

12. The apparatus of claim 7 wherein said means for comparing said dc voltage level with a dc reference voltage level is determining whether said dc voltage level of said rf energy is higher, lower or equal to said dc reference voltage value, thereby providing an electrical signal that reflects the outcome of said determination, said electrical signal being indicative of the result of said compare being either a higher compare or an equal compare or a lower compare.

* * * * *